United States Patent (12)
Young et al.

(10) Patent No.: US 8,057,501 B2
(45) Date of Patent: Nov. 15, 2011

(54) COLLAPSIBLE LANCING DEVICE

(75) Inventors: Kevin Young, Boston, MA (US); Maiya Shur, Reston, VA (US); Gaurav Rohatgi, Franklin, MA (US); Damien Vizcarra, Pasadena, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 570 days.

(21) Appl. No.: 12/197,518

(22) Filed: Aug. 25, 2008

(65) Prior Publication Data

US 2010/0049232 A1    Feb. 25, 2010

(51) Int. Cl.
*A61B 17/14* (2006.01)
(52) U.S. Cl. ........................................... 606/182
(58) Field of Classification Search .................. 606/181, 606/182, 183; 604/136, 137, 138, 139; 600/583; 30/143, 151, 153, 154, 155, 156, 157, 158, 30/159, 160, 161
See application file for complete search history.

(56) References Cited

U.S. PATENT DOCUMENTS

| 4,577,630 | A | 3/1986 | Nitzsche et al. |
| 5,971,941 | A | 10/1999 | Simons et al. |
| 6,136,013 | A | 10/2000 | Marshall et al. |
| 7,377,904 | B2 | 5/2008 | Conway et al. |
| 2006/0100656 | A1 | 5/2006 | Olson et al. |

| 2007/0078360 | A1* | 4/2007 | Matsumoto et al. .......... 600/583 |
| 2008/0058847 | A1 | 3/2008 | Abe et al. |
| 2008/0200782 | A1 | 8/2008 | Planman et al. |

FOREIGN PATENT DOCUMENTS

| EP | 1 552 788 A1 | 7/2005 |
| EP | 1779780 A2 | 5/2007 |
| WO | 2007/059048 A1 | 5/2007 |
| WO | 2008/009782 A2 | 1/2008 |

OTHER PUBLICATIONS

PCT International Search Report (Date of Mailing: Jan. 13, 2010); PCT/US2009/054385, filed Aug. 20, 2009.

* cited by examiner

*Primary Examiner* — Ryan Severson
*Assistant Examiner* — Jonathan W Miles
(74) *Attorney, Agent, or Firm* — Young Basile (57) ABSTRACT

A lancing device for use with a removable lancet having a sharp tip. The lancet includes a housing. The lancing device can include a handle connected to the housing for movement between a storage position, where the housing and handle are configured to be compactly stowed, and a use position, where the housing and handle are configured to be grasped by a user to perform the piercing operation. The lancing device can include an opening formed in the housing and a tray that is moveable with respect to the housing between an open position, where the lancet can be installed on or removed from the tray, and a closed position, where the lancet can be utilized to perform a piercing operation. The lancing device can include a structure moveable with respect to the housing between a first position, where a first piercing aperture is defined, and a second position, where a second piercing aperture is defined, where the second piercing aperture is larger than the first piercing aperture.

17 Claims, 12 Drawing Sheets

COLLAPSIBLE LANCING DEVICE

BACKGROUND

Lancing devices are typically handheld units that permit users to draw blood for testing and diagnostic purposes. These devices include a housing with a piercing aperture, a lancet that contains one or more needles, and a firing mechanism. The firing mechanism typically includes a spring or other biasing means which can be cocked either by insertion of the lancet or by pulling a cocking handle, for example. Once the lancing device is cocked, it is placed against the user's skin, often the fingertip. The user can then press a trigger to actuate the firing mechanism, which momentarily drives the sharp tip of the needle through the piercing aperture to puncture the user's skin and draw blood. When the lancing operation is complete, the user can press a second actuator to eject the lancet for removal and disposal. A consideration is the design of lancets and lancet devices is to minimize parts and thus minimize cost of production.

A consideration in the design of lancets is to minimize the discomfort experienced by users during the lancing process. To this end, some lancing devices include mechanisms to adjust the distance that the needle sharp protrudes through the piercing aperture, thus regulating the depth that the needle penetrates the user's skin. In some cases, these depth adjustment mechanisms include adjustable stops that limit the forward movement of the lancet during firing. In other cases, depth adjustment mechanisms adjust the tip of the lancing device to reduce or increase the distance that the needle sharp protrudes from the lancing device. One approach for depth adjustment is illustrated in U.S. Pat. No. 5,984,940. A lancet holder is moved axially within a lancing device housing to move the needle closer to or farther away from the piercing aperture, thus adjusting penetration depth.

Another consideration in the design of lancing devices is to avoid accidental needle pricks when inserting and removing lancets from the lancing device. To this end, lancets include safety features such as frangible tabs which cover the needle sharp prior to insertion in the lancing device. Once the lancet is inserted, the use can break off and remove the frangible tab. Some lancets also include sleeves coaxially mounted to the main body of the lancet. The sleeve can be positioned so that it protectively encloses the needle sharp. During the lancing operation, the main body of the lancet slides through the sleeve to expose the lancet sharp. After removal of the lancet, however, the sleeve can be locked in its protective position, reducing the likelihood that a person handling the use lancet will prick himself or herself.

It has also been proposed that a reference member be attached to the lancet itself. During incision, the lancet and the reference member are moved together toward the piercing aperture to effectively narrow the piercing aperture. After incision, the reference member and the lancet are retracted to leave the piercing aperture unobstructed. Prior to the lancet's insertion into the lancing device, the reference member can be adjusted relative to the lancet for purposes of regulating the penetration depth of the needle.

Another consideration in the design of lancing systems is the ease with which a lancet can be inserted into the lancing device. It is known that when a lancet is inserted into a lancing device, the force of the insertion can be used to cock the device. However, if the device is already cocked, and a lancet was to be inserted, there is some risk that the device would discharge during the insertion process and the user would be accidentally pricked. It is also known to provide a removable cap on the housing to permit insertion of the lancet. However, this requires an additional step in the process (namely, removing the cap).

Another consideration in the design of lancets is to minimize the handling of the lancet by the user during ejection of the lancet from the lancing device. To this end, it is known to provide ejection mechanisms that include a sliding member that engages the lancet to push it out of the lancing device. In such cases, it is helpful to restrain the lancet carrier from forward movement. Known mechanisms for achieving this use the sliding member to actuate a releasable connector to engage the lancet carrier and prevent its forward movement, as shown for example in U.S. Pat. No. 6,197,040. The releasable connector is biased towards the ejection slide and away from the lancet carrier and is configured so that when the lancet carrier is urged forward, a force vector is transmitted through the connector to the ejection slide. This means that the slide and the ejector rub against each other with a degree of force, causing friction that is discernable to the user.

SUMMARY

Lancing devices and methods of use are provided. In accordance with some embodiments of the invention, a lancing device for use with a lancet having a sharp tip includes a housing and a handle. The housing has an interior space in which the lancet can be received. The handle is connected to the housing for movement between a storage position, where the housing and the handle are configured to be compactly stowed, and a use position, where the housing and the handle are configured to be grasped by a user to perform a piercing operation.

The lancing device could include a piercing aperture, where the handle substantially blocks the piercing aperture in the storage position. The housing and the handle can cooperate to define a first length in the storage position and a second length in the use position.

In other embodiments, the handle could overlie at least part of the housing in the storage position to prevent insertion or removal of the lancet from the interior space. More particularly, the lancing device could include an opening in the housing and a tray that is receivable within the opening and on which the lancet can be removably retained, where the handle overlies at least part of the opening in the storage position to prevent removal of the tray from the housing.

In additional embodiments, the handle is pivotally connected to the housing for movement between the storage position and the use position. In particular, the lancing device could include a pivot joint formed at a first end of the housing, wherein the handle has a first leg pivotally connected to the housing by the pivot joint, a second leg pivotally connected to the housing by the pivot joint, and a third leg that spaces the first leg and the second leg, where the third leg is disposed at a second end of the housing in the storage position.

In other embodiments, the lancing device could include a structure moveable with respect to the housing between a first position, where a first piercing aperture is defined, and a second position, where a second piercing aperture is defined, and the second piercing aperture is larger than the first piercing aperture. In embodiments where the lancing device includes a tray, the structure could be connected to the tray for movement between a first position, where the tray and the structure cooperate to define a first piercing aperture, and a second position, where the tray and the structure cooperate to define a second piercing aperture, the second piercing aperture larger than the first piercing aperture.

In embodiments where the lancing device includes a tray, the tray can be moveable with respect to the housing between an open position, where the lancet can be installed on or removed from the tray, and a closed position, where the lancet can be utilized to perform a piercing operation. The tray can have an end wall, and a piercing aperture can be formed through end wall, wherein the end wall of the tray substantially occupies the opening of the housing when the tray is in the closed position.

In other embodiments of the lancing device, the lancet includes a cap configured to cover the sharp tip and the lancing device has at least one engaging member that engages the cap of the lancet when the tray is moved from the open position to the closed position, wherein engagement of the engaging member with the cap removes the cap from the sharp tip of the lancet.

In yet other embodiments, the lancing device includes a carrier block that is engageable with the lancet to cover the sharp tip of the lancet. The carrier block has a first engaging structure configured to allow disengagement of the lancet and the carrier block during installation of the lancet with respect to the lancing device. The carrier block also has a second engaging structure configured to permit engagement of the lancet and the carrier block during removal of the lancet from the lancing device and restrain the lancet against subsequent disengagement from the carrier block. The lancing device could also include an engaging member that is slidably connected to the housing and engageable with the lancet to remove the lancet from the first engaging structure of the carrier block.

BRIEF DESCRIPTION OF THE DRAWINGS

The description herein makes reference to the accompanying drawings wherein like reference numerals refer to like parts throughout the several views, and wherein.

DETAILED DESCRIPTION OF THE EMBODIMENTS

FIGS. 1-3C show an example of a lancing device 100 for use with a removable lancet 101a having a sharp tip 101b. The lancing device 100 includes a housing 103, a handle 104, a skin engaging end 110, a piercing aperture 120, and an operating button 112 that actuates a firing mechanism 114 to perform a piercing operation of the lancing device 100. The lancing device 100 is operated by a user to draw a sample of blood or other bodily fluid from the user's body such as for diagnostic purposes, by propelling the sharp tip 102 of the lancet 101 into engagement with a portion of the user's body.

Figure 1:
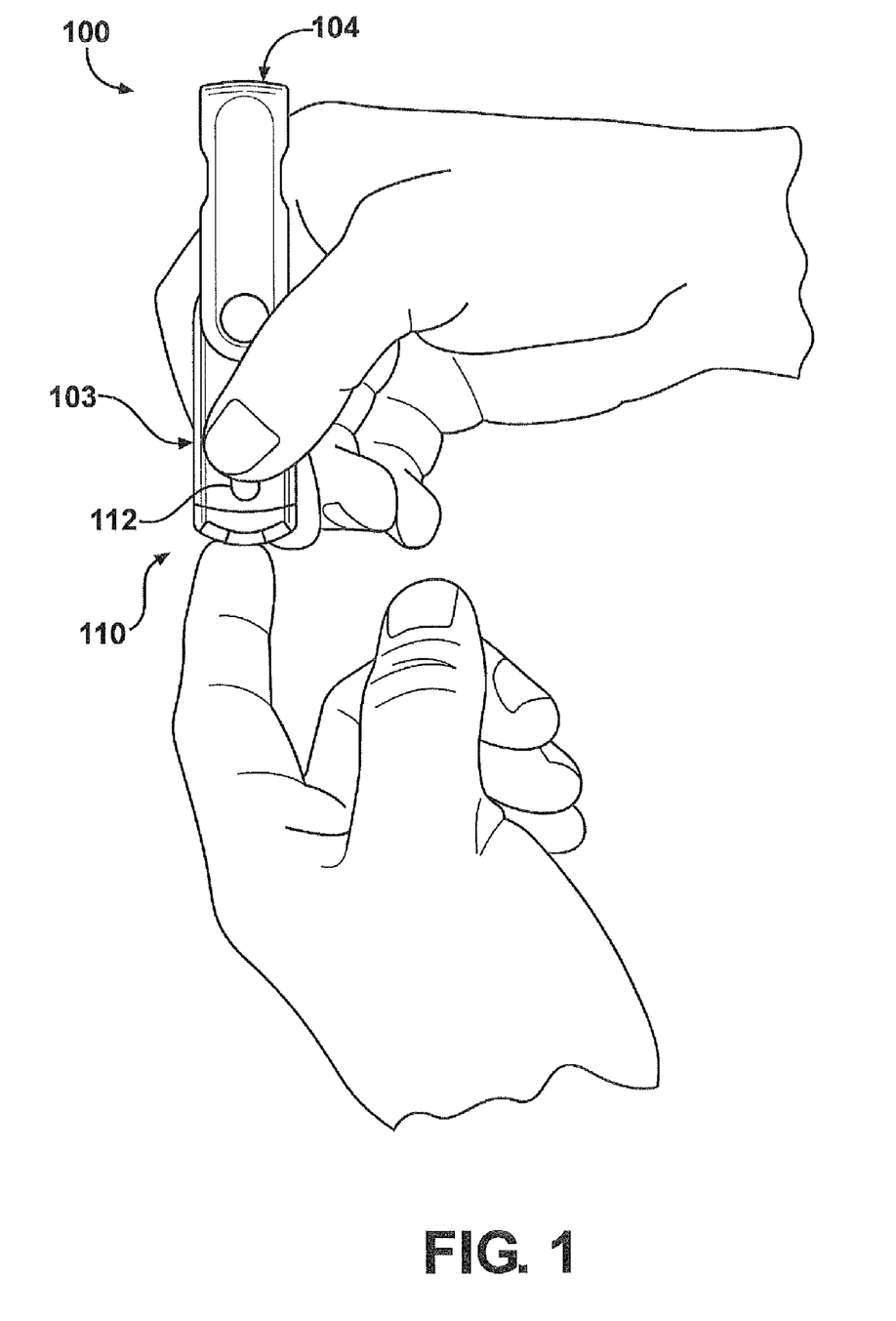
FIG. 1 is a perspective view of a lancing device in a use position in accordance with an embodiment of the invention.
Figure 2A:
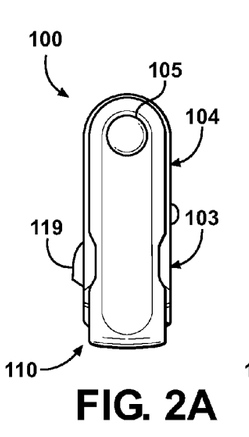
FIG. 2A is a front view showing the lancing device of FIG. 1 in a storage position.
Figure 2B:
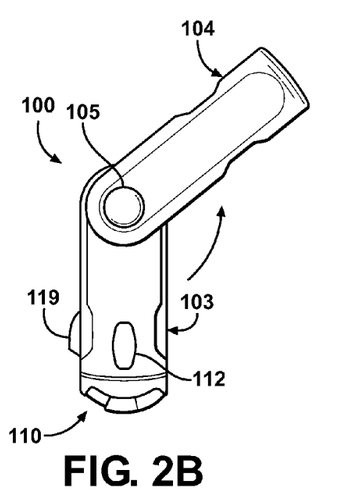
FIG. 2B is a front view showing the lancing device of FIG. 1 in an intermediate position.
Figure 2C:
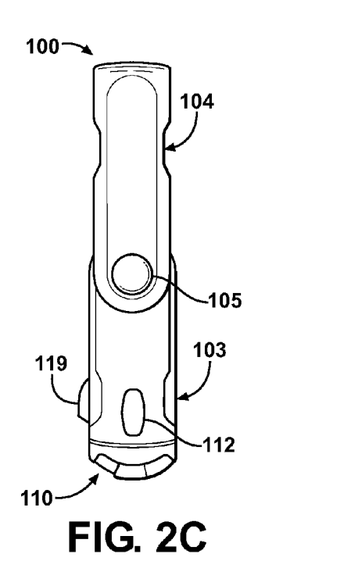
FIG. 2C is a front view showing the lancing device of FIG. 1 in a use position and a tray of the lancing device is in a closed position.

The handle 104 of the lancing device 100 can be connected to the housing 103 for movement between a storage position, shown in FIG. 2A, and a use position, shown in FIG. 2C. In the storage position, the lancing device 100 is configured to be compactly stowed. In the use position, the housing 103 and the handle 104 are configured to be grasped by the user to perform the piercing operation. The housing 103 and the handle 104 cooperate to define a first length in the storage position and a second length in the use position, where the combined length of the housing 103 and the handle 104 is longer in the use position than in the storage position. The connection between the housing 103 and the handle 104 can be accomplished using any structure suitable to allow movement between the storage and use positions, and can include connecting structures that permanently attach the handle 104 to the housing 103, as well as structures that allow selective detachment of the handle 104 and the housing 103.

For example, to connect the handle 104 to the housing 103, a pivot joint 105 can be provided on the handle 104 opposite the end portion 110. The pivot joint 105 is connected to both the handle 104 and the housing 103 to allow the handle 104 to pivot with respect to the housing 103 between the storage and use positions, as shown in FIG. 2B. Alternative structures for connecting the handle 104 to the housing 103 can include, but are not limited to, a folding joint, a sliding connection, a telescoping connection and a friction fit.

The handle 104 can be configured to prevent completion of the piercing operation when the handle 104 is in the storage position. For example, the handle 104 can be configured to overlie and thus block access to the piercing aperture 120, or the handle 104 can be configured to overlie and thus block access to the operating button 112 to prevent accidental actuation of the lancing device 100.

Figure 2D:
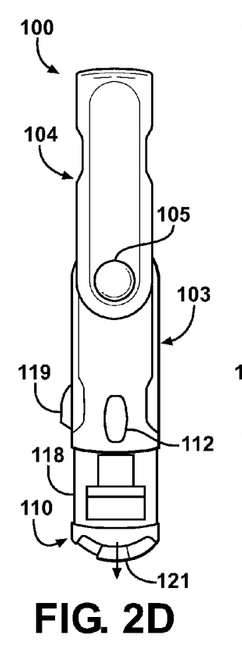
FIG. 2D is a front view showing the lancing device of FIG. 1 in a use position, and the tray of the lancing device is in an open position.
Figure 2E:
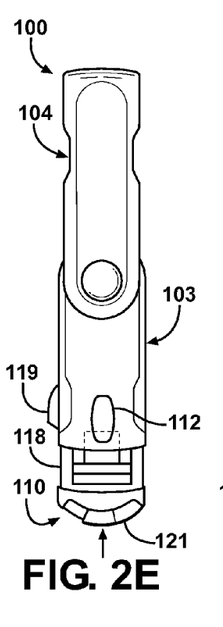
FIG. 2E is a front view showing the lancing device of FIG. 1 in a use position, and the tray of the lancing device is moving from the open position to the closed position.

The lancing device 100 includes a tray 118 that is receivable within an opening 116 formed in the housing for movement between a closed position, shown in FIG. 2C, to an open position, shown in FIGS. 2D and 2E. Thus, the handle 104 can be configured to prevent insertion and removal of the lancet 101, by overlying the tray 118 to prevent the tray 118 from moving from the closed position to the open position. A thumb button 119 can be connected to the tray 118 and extend through the housing 103 to facilitate movement of the tray 118 between the open and closed positions.

Figure 2F:
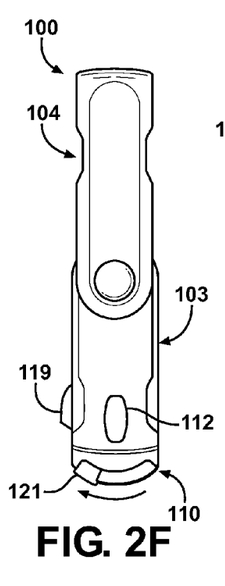
FIG. 2F is a front view showing the lancing device of FIG. 1 in a use position, a tray of the lancing device is in a closed position, and an aperture defining structure has been moved to an AST position.

As shown in FIG. 2F, the lancing device 100 can include a piercing aperture defining structure 121 that is moveable to change the size of the piercing aperture 120, as will be explained in detail in connection with the lancing device of FIG. 13.

Figure 2G:
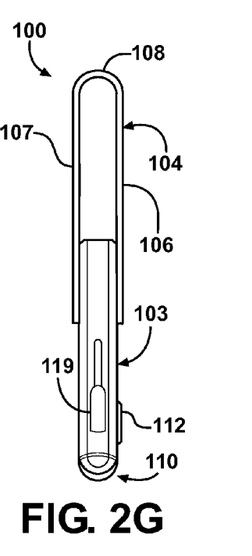
FIG. 2G is a side view showing the lancing device of FIG. 1 in the use position.

In an exemplary configuration, the handle 104 has a first leg 106 that is connected to the pivot joint 105, a second leg 107 that is opposite the first leg 106 and connected to the pivot joint 105, and a third leg 108 that is perpendicularly connected to the first leg 106 and the second leg 107 to space the first leg 106 from the second leg 107, as shown in FIG. 2G. In the storage position, the first leg 106 substantially overlies the operating button 112, while the third leg 108 substantially overlies the end portion 110 of the housing 103 and the piercing aperture 120.

Figure 3A:
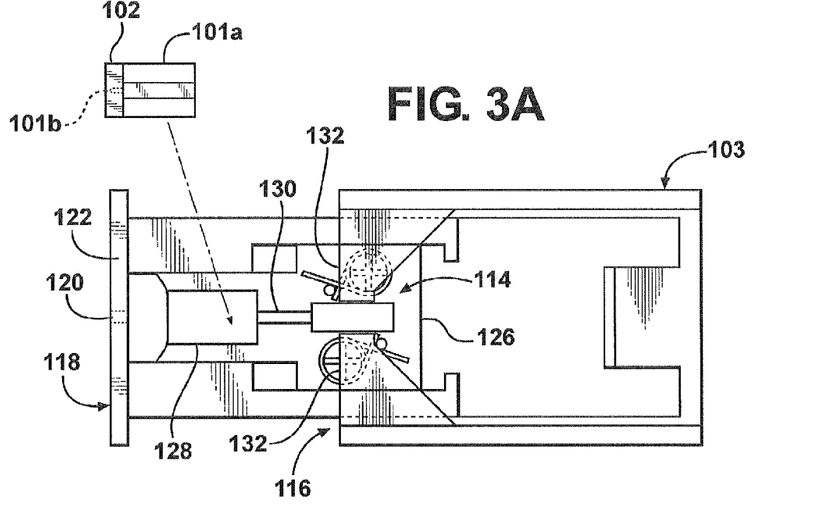
FIG. 3A is a top, cut-away view of the housing of the lancing device of FIG. 1.
Figure 3B:
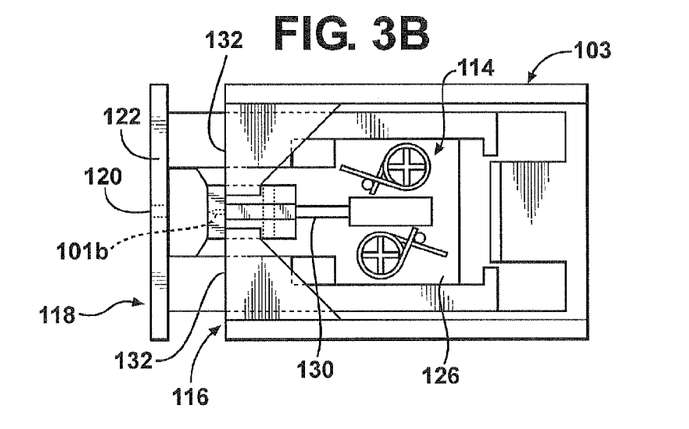
FIG. 3B is a top, cut-away view of the housing of the lancing device of FIG. 1.
Figure 3C:
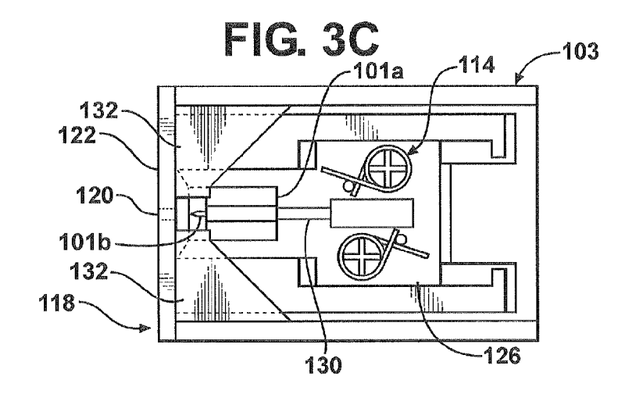
FIG. 3C is a top, cut-away view of the housing of the lancing device of FIG. 1.

As best seen in FIGS. 3A-3C, the tray 118 includes a outer portion 124 having an end wall 122, through which the piercing aperture 120 extends. A base portion 126 of the tray 118 is slidably related to the outer portion 124 of the tray 118 for receiving the lancet 101a, and the firing mechanism 114 is disposed on the base portion 126 of the tray 118.

The lancing device 100 provides for automatic removal of the cap 101a from the sharp tip 101b of the lancet 102 during movement of the tray 118 from the open position to the closed position. Initially, the tray 118 is in the open position, the cap 102 is disposed on the sharp tip 101b of the lancet 101a, and the lancet 101a is not disposed of the tray 118, as shown in FIG. 3A. Installation begins by placing the lancet 101a in a lancet recess 128 that is provided on the base portion 126 of the tray 118 and in engagement with a firing rod 130 of the firing mechanism 114.

With the lancet 101a in place on the base portion 126 of the tray 118, installation continues by moving the tray 118 toward the closed position. As the tray 118 moves inward, the base portion 126 and the outer portion 124 of the tray 118 move substantially in unison, and slide under a pair of arms 132 of the housing 103 that extend inward from the lateral sides of the housing 103 near the opening 116 of the housing 103.

After the lancet 101a passes under the arms 132 of the housing 103, the cap 102 come into engagement with the arms 132, as shown in FIG. 3B, since the cap 102 is formed having a height that is greater than the remainder of the lancet 101a. Since the lancet 101a is secured to the base portion 126 of the tray 118 by the firing rod 130, continued movement of the tray 118 toward the closed position removes the cap 102 from the sharp tip 101b of the lancet 101a, as shown in FIG. 3C. When the tray 118 reaches the closed position, the cap 102 drops either out of the housing 103 or into a storage compartment that is formed in the housing 103.

In an alternative embodiment, the invention provides a lancing device 200 that includes a carrier block 240 that facilitates installation and removal of a lancet 201 having a sharp tip 202, as shown in FIGS. 4-7B. A housing 203 of the lancing device 200 includes an opening 218 that is in communication with an open space defined within the housing 203 and a tray 220 that is receivable within the opening 218. The tray 220 is moveable with respect to the housing 203 between an open position, where the lancet 201 can be installed on or removed from the tray 220, and a closed position, where the lancet 201 can be utilized to perform the piercing operation.

Figures 6A, 6B:
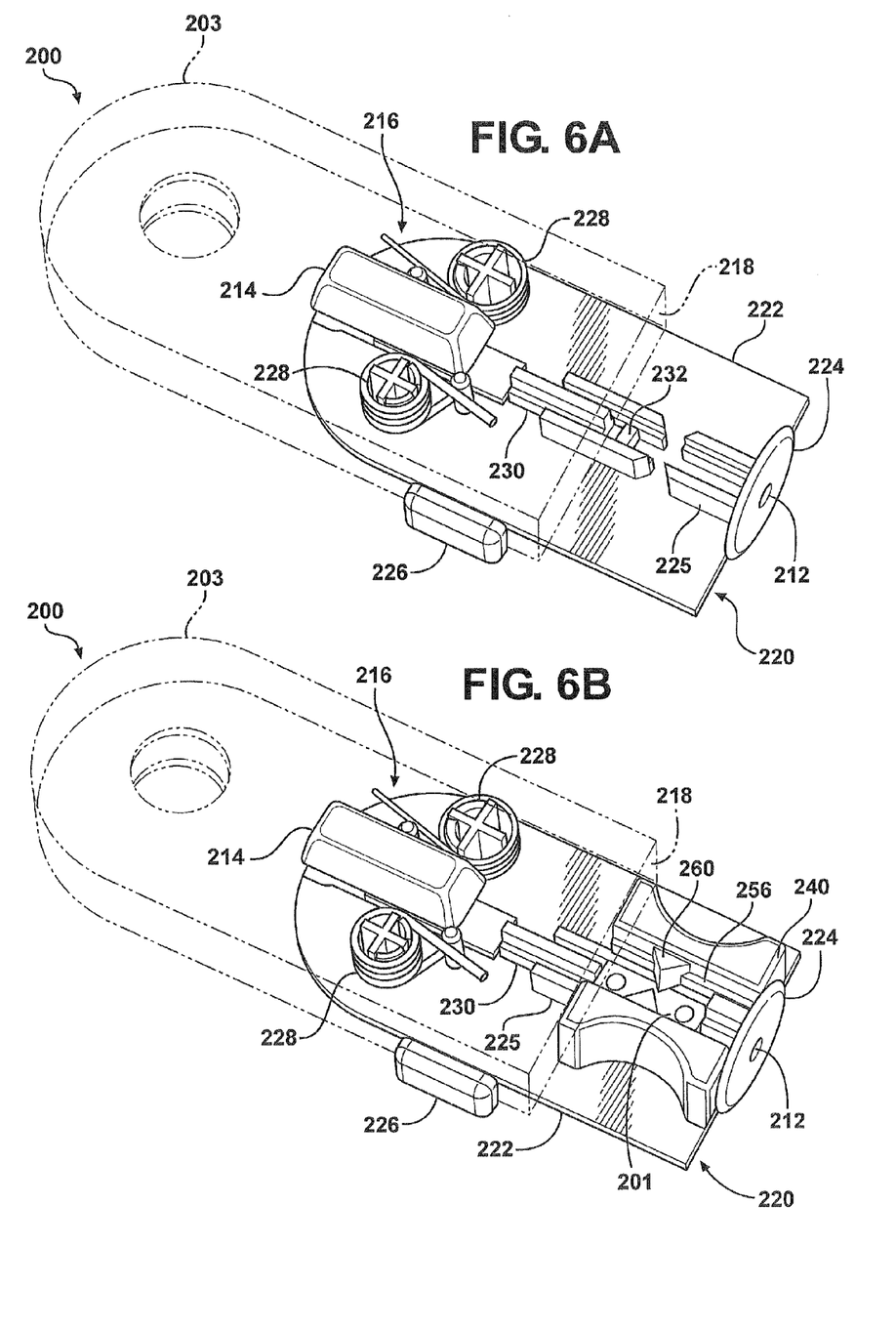
FIG. 6A is a perspective view of a lancing device in accordance with an embodiment of the invention, showing a tray in an open position prior to installation of the lancet.
FIG. 6B is a perspective view of a housing of the lancing device of FIG. 6A showing the tray in the open position and the carrier block disposed on the tray during installation of the lancet with a firing mechanism in a neutral position.

The tray 220 includes a base portion 222 and an end wall 224. The lancet 201 is configured to be removably retained on the base portion 222 of the tray 220. The end wall 224 can extend substantially perpendicular to the base portion 222 so that the end wall 224 substantially occupies the opening 218 in the housing 203 when the tray 220 is in the closed position. The piercing aperture 212 can be formed through the end wall 224. A substantially u-shaped track 225 is formed on the tray 220, extends substantially perpendicular to the end wall 224, and terminates at the end wall 224 adjacent to the piercing aperture 212. The track 225 is configured to support the lancet 201 above the tray 220 and guide the lancet 201 toward the piercing aperture 212 during the piercing operation. A thumb button 226 can be fixedly connected to the tray 220 and extend through a slot in the housing 203 to provide a convenient surface that the user can engage to move the tray 220 between the open and closed positions.

A firing mechanism 216 is disposed on the tray 220, and is operatively connected to the operating button 214. The firing mechanism 216 includes one or more biasing elements 228, such as springs, and a firing rod 230 having an engaging member 232, such as a hook, that is engageable with the lancet 201 to propel the lancet 201 during the piercing operation. The operating button 214 is configured to move the firing mechanism 216 from a neutral position, where the biasing elements 228 do not exert a biasing force on the firing rod 230, to a cocked position, where the biasing elements 228 exert a biasing force on the firing rod 230 while the firing mechanism 216 restrains the firing rod 230 from moving in response to the biasing force exerted by the biasing elements 228. When the firing mechanism 216 is in the cocked position, the operating button 214 can be actuated to release the firing 230 to perform the piercing operation in response to the force of the biasing elements 228.

Figure 7A:
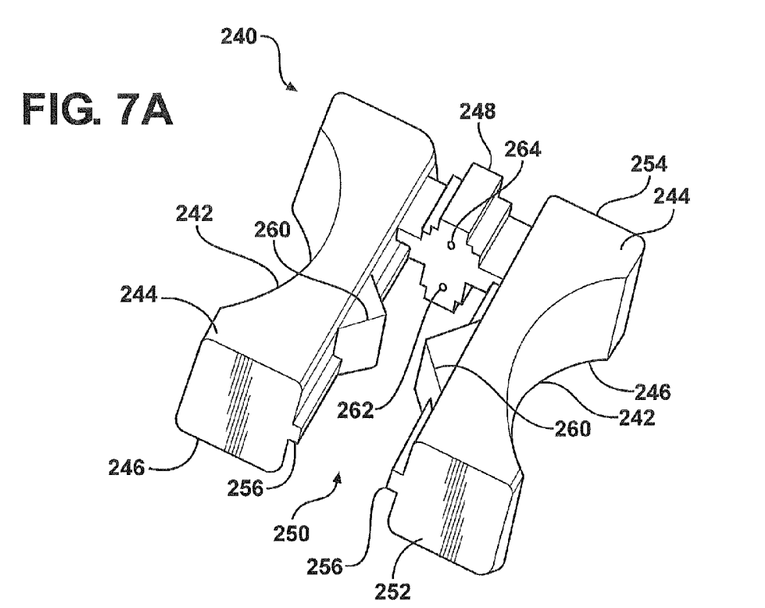
FIG. 7A is a perspective view of the carrier block.
Figure 7B:
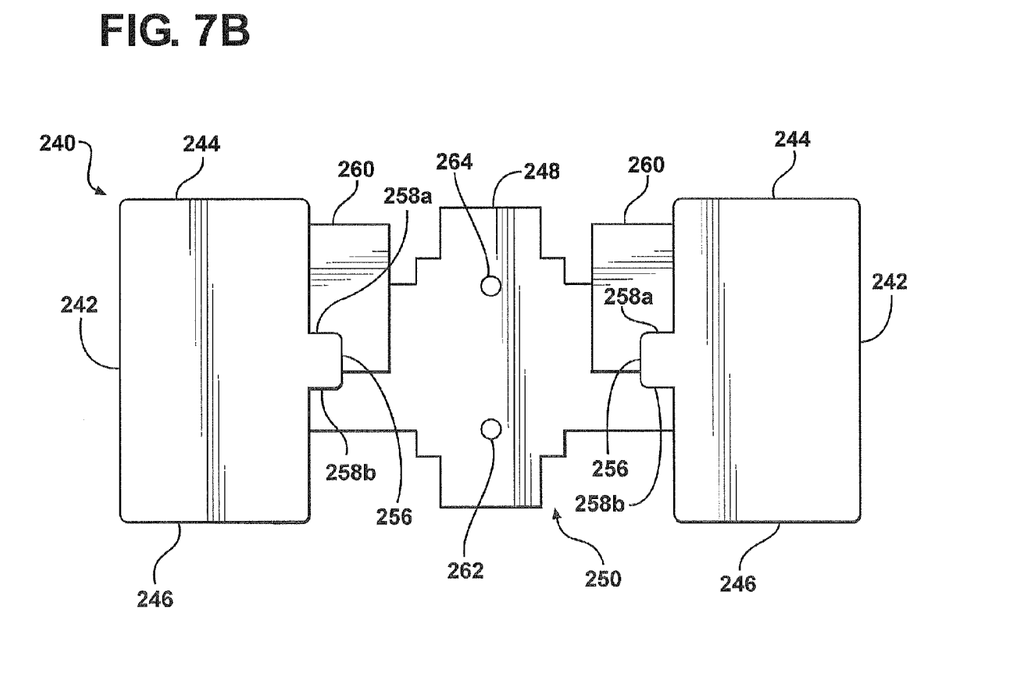
FIG. 7B is an end view of the carrier block.

As shown in FIGS. 7A-7B, the carrier block 240 is a unitary body that includes a pair of opposed side portions 242 each having top surfaces 244 and bottom surfaces 246 The opposed side portions 242 are spaced from one another by a bridge portion 248 to form an open space 250 between the opposed side portions 242. The open space 250 extends from an open end 252 of the carrier block 240 to the bridge portion 248, which is located at a closed end 254 of the carrier block 240.

Adjacent to the open space 250 of the carrier block 240, a substantially rectangular longitudinal projection 256 extends inward from each side portion 242, from the open end 252 of the carrier block 240 to the bridge portion 248. Each projection 256 has an upward-facing shoulder 258a and a downward-facing shoulder 258b.

To engage the lancet 201, as will be explained herein, the carrier block 240 includes a pair of engaging structures 260. Each engaging structure 260 is formed on a respective side portion 242 of the carrier block 240 at an intermediate location between the open end 252 and the closed end 254 of the carrier block 240, and extends into the open space 250. The engaging structures 260 extend from the projections 256 toward the upper surfaces 244 of the side portions 242, and terminate at or below the upper surfaces 244.

To receive and enclose the sharp tip 202 of the lancet 201 prior to use, a lower aperture 262 is provided in the bridge portion 248 of the carrier block 240, facing the open space 250. To receive and enclose the sharp tip 202 of the lancet 201 after use, an upper aperture is provided in the bridge portion 248 of the carrier block 240, facing the open space 250. Thus, in a pre-use condition, the sharp tip 202 of the lancet 201 is disposed un the lower aperture 262 of the carrier block 240, and in a post-use condition, the sharp tip 202 of the lancet 201 is disposed in the upper aperture 262 of the carrier block 240.

Referring back to FIGS. 6A-6H, installation and removal of the lancet 201 with respect to the lancing device 200 will be explained. To allow installation of the lancet, the tray 220 is first moved to the open position, as shown in FIG. 6A, and the firing mechanism is in the neutral position.

Figure 4:
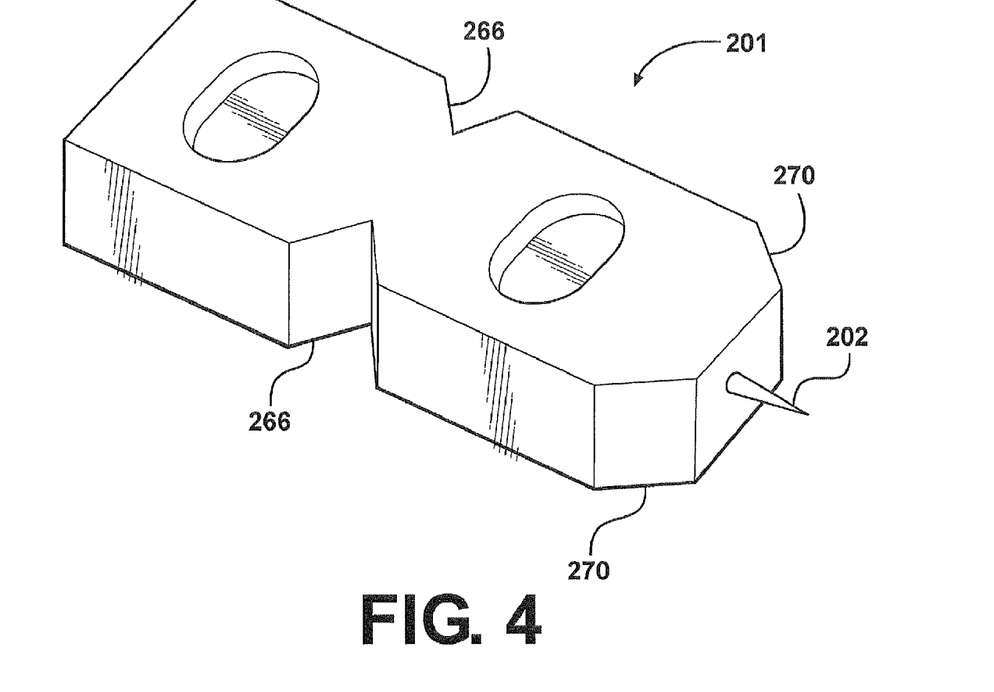
FIG. 4 is a perspective view of a lancet.
Figure 5:
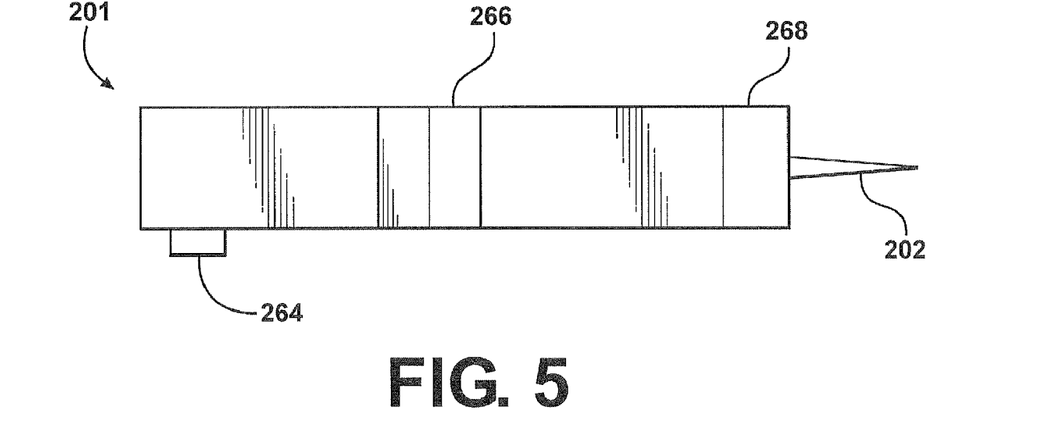
FIG. 5 is a side view of the lancet of FIG. 4.

Next, a carrier block 240 and lancet 201 in the pre-use condition are placed on the tray 220, so that the bottom surfaces 246 of the side portions 242 of the carrier block 240 face the tray, as shown in FIG. 6B. With reference to FIGS. 4-5, it is noted that the lancet 201 includes and a projection 264 that is formed on a lower side of the lancet 201, and a pair of opposed notches 266 that are formed on the lateral sides of the lancet 201. In the pre-use condition, the lancet 201 is disposed within the carrier block 240 such that the projection 264 is oriented toward the bottom surfaces 246 of the side portions 242 of the carrier block 240, and thus the projection 264 faces the tray 220 during installation of the lancet 201. Accordingly, the lancet 201 is received on the track 225 of the tray 220 and the projection 264 of the lancet 201 engages the hook 232 of the firing rod 230.

Figure 6C:
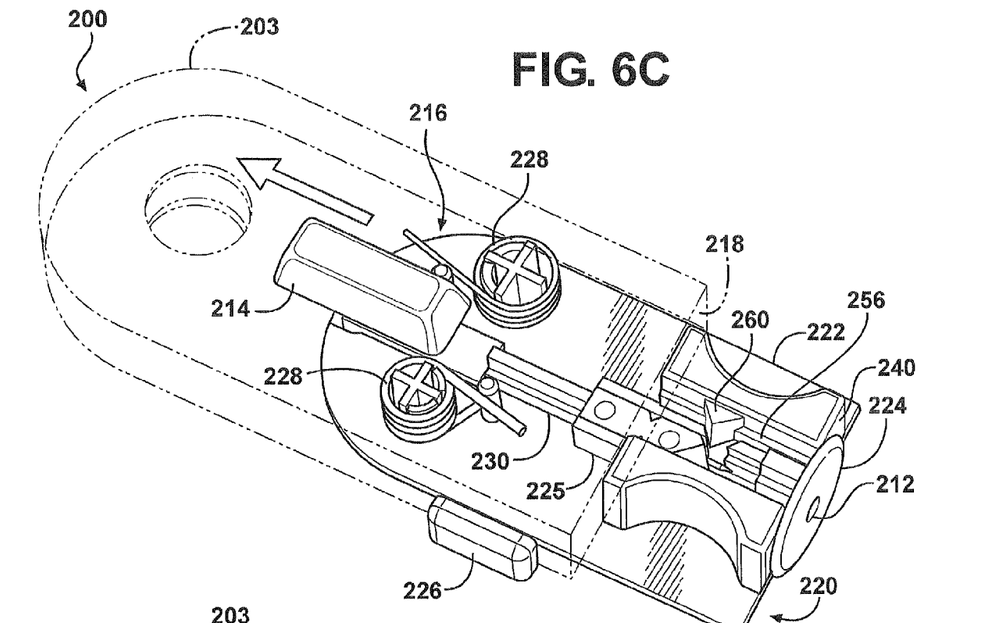
FIG. 6C is a perspective view of a housing of the lancing device of FIG. 6A showing the tray in the open position and the carrier block disposed on the tray during installation of the lancet with the firing mechanism in a cocked position.
Figure 6D:
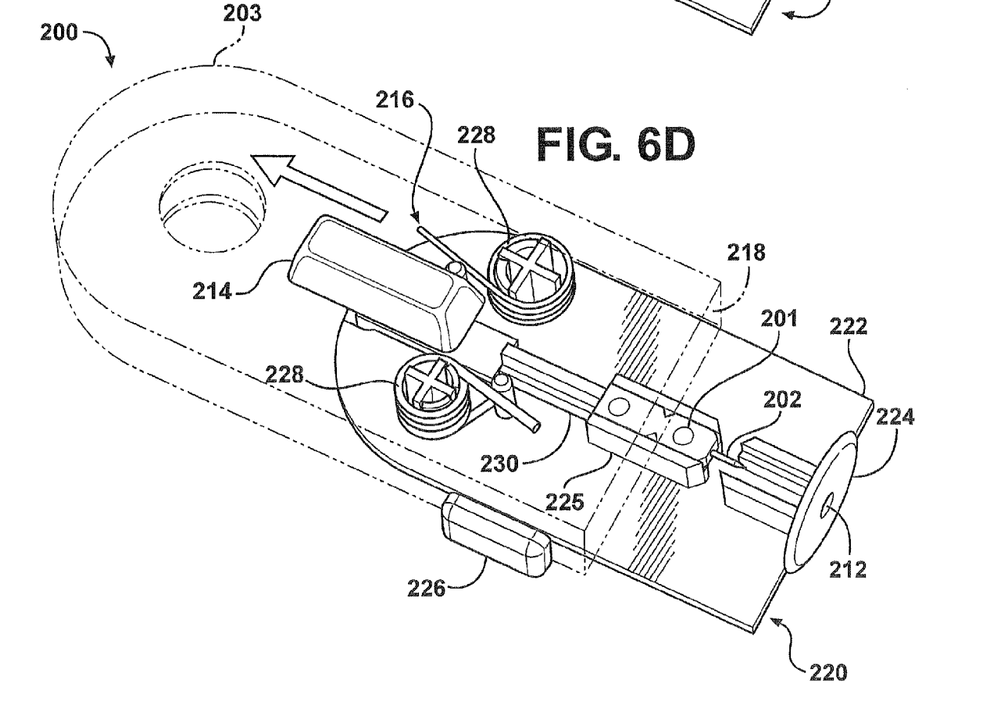
FIG. 6D is a perspective view of a housing of the lancing device of FIG. 6A showing the tray in the open position and the lancet engaged with the firing rod of the firing mechanism during installation of the lancet with the firing mechanism in the cocked position.

To remove the lancet 201 from the carrier block 240, the user moves the firing mechanism 226 to the cocked position using the operating button 214, as shown in FIG. 6C. In the pre-use condition, the lancet 201 is retained in connection with the carrier block 240 by disposition of the sharp tip 202 of the lancet 201 in the lower aperture 262 of the carrier block 240. Since the lancet 201 is located in the open space 250 below the longitudinal projections 256, the notches 266 of the lancet 201 are not engaged with the engaging structures 260 of the carrier block 240, and thus, the engaging structures 260 do not restrain removal of the lancet 201 from the carrier block 240 in the pre-use condition. Thus, with the firing mechanism 216 in the cocked position, the lancet 201 is separated from the carrier block 240, and the carrier block 240 can be removed from the tray 220, as shown in FIG. 6D.

Figure 6E:
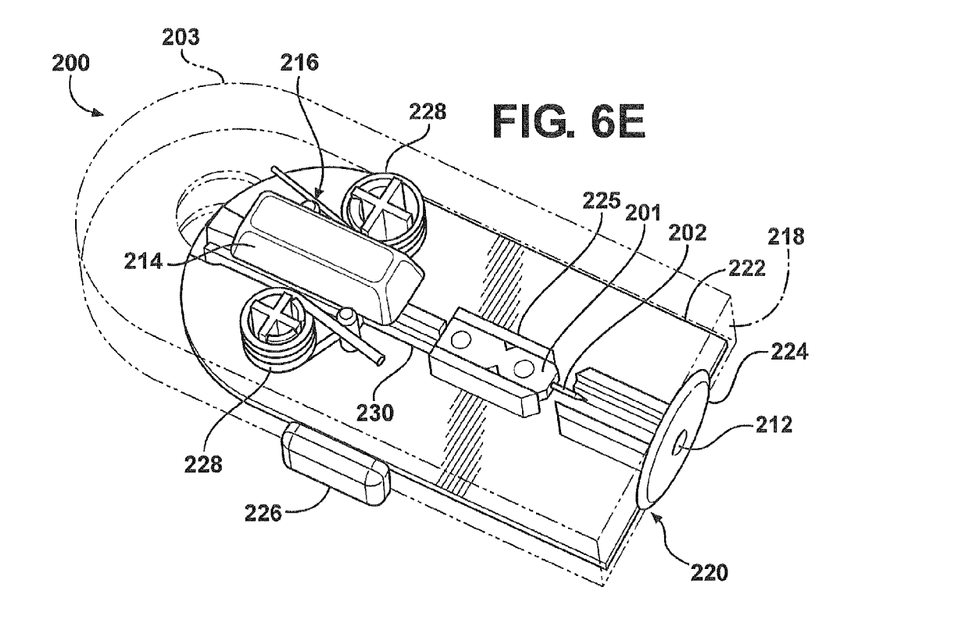
FIG. 6E is a perspective view of a housing of the lancing device of FIG. 6A showing the tray in a closed position and the lancet engaged with the firing rod of the firing mechanism with the firing mechanism in the cocked position.

Before the piercing operation can be performed using the lancing device 200, the tray 220 is moved from the open position to the closed position, as shown in FIG. 6E. The piercing operation can then be performed by engaging the piercing aperture 212 with the user's skin, and actuating the operating button 214.

Figure 6F:
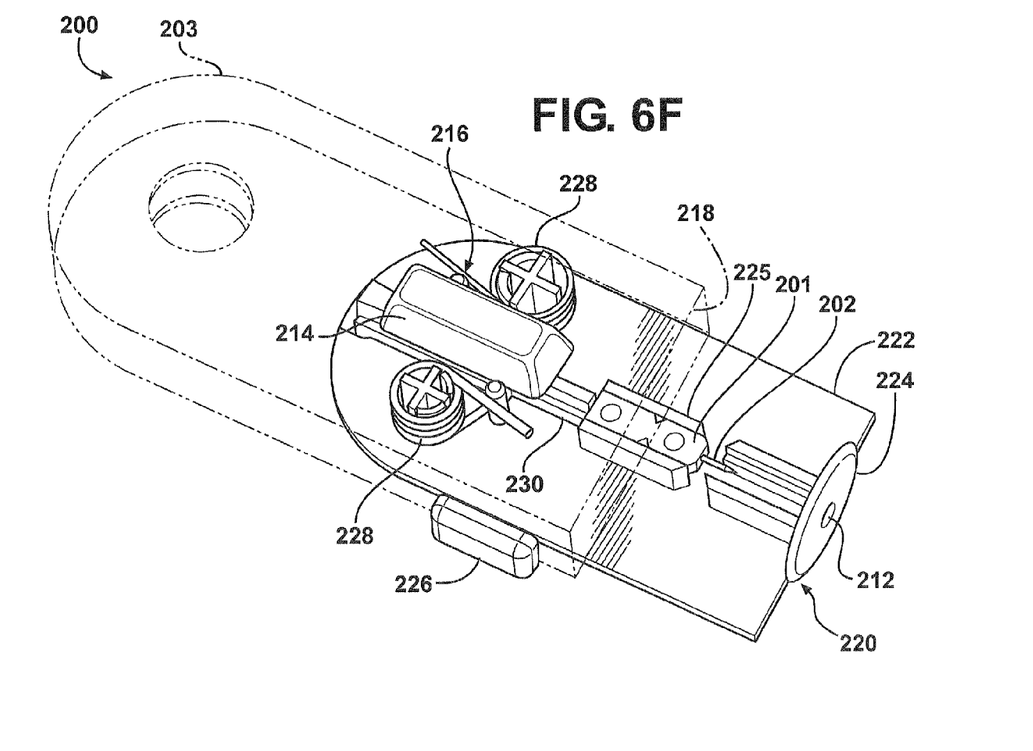
FIG. 6F is a perspective view of a housing of the lancing device of FIG. 6A showing the tray in the open position and the lancet engaged with the firing rod of the firing mechanism during removal of the lancet with the firing mechanism in the cocked position.

After the piercing operation has been completed, the used lancet 201 can be removed from the lancing device 200. In order to do so, the tray 220 is moved from the closed position to the open position and the firing mechanism 216 is moved to the cocked position using the operating button 214, as shown in FIG. 6F.

Figure 6G:
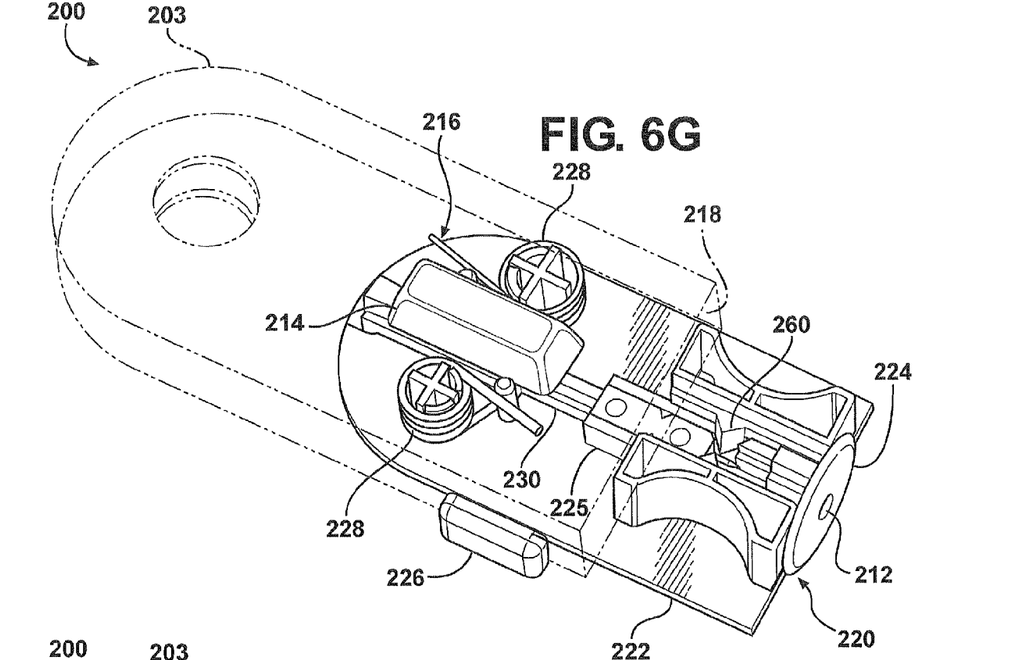
FIG. 6G is a perspective view of a housing of the lancing device of FIG. 6A showing the tray in the open position and the carrier block disposed on the tray prior to connection of the lancet with the carrier block during removal of the lancet.

With the firing mechanism 216 in the cocked position, clearance is provided so that the carrier block 240 can be placed on the tray 220, as shown in FIG. 6G. The carrier block 240 is placed with the upper surfaces 244 of the side portions 242 facing the tray 220, and the engaging structures 260 of the carrier block 240 are received in openings 268 that are formed through the track 225 to align the carrier block 240 with respect to the tray 220.

Figure 6H:
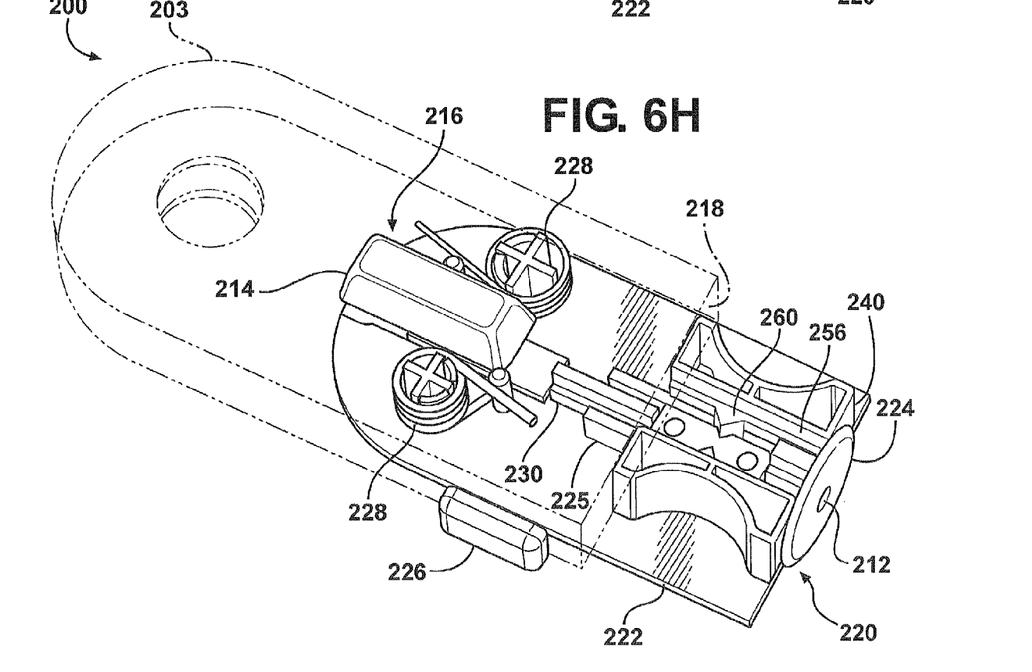
FIG. 6H is a perspective view of a housing of the lancing device of FIG. 6A showing the tray in the open position and the carrier block disposed on the tray prior to connection of the lancet with the carrier block during removal of the lancet.

To replace the used lancet 201 in the carrier block 240, the user moves the firing mechanism 216 to the neutral position using the operating button 214. As the firing mechanism 216 moves toward the neutral position, the firing mechanism moves the lancet 201 into engagement with the engaging structures 260 of the carrier block 240. As the lancet 201 continues moving into the carrier block 240 pair of chamfered corners 270 that are formed on the lancet 201 engage the engaging structures 260 of the carrier block 240 to resiliently spread the side portions 242 of the carrier block 240 away from one another. When the engaging structures 260 of the carrier block 240 reach the notches 266 of the lancet 201, the side portions 242 of the carrier block 240 return to their normal position with respect to one another and the engaging structures 260 engage the notches 266 of the lancet 201, as shown in FIG. 6H. At the same time, the sharp tip 202 of the lancet enters the upper aperture 264 that is formed in the bridge portion 248 of the carrier block 240.

It should be understood that the change in position of the lancet 201 in the carrier block 240 prevents accidental reuse of a previously used lancet 201. In particular, since the engaging structures 260 of the carrier block 240 are engaged with the notches 266 of the lancet 201 when the lancet 201 and the carrier block 240 are in the post-use condition, the lancet 201 is restrained against separating from the carrier block 240 in response to movement of the firing mechanism 216 toward the cocked position from the neutral position.

In an alternative embodiment, the invention provides a lancing device 300 that includes a decapping mechanism 302 for use with a lancet 304 having a cap 306 that covers a sharp tip 308 of the lancet 304, as shown in FIGS. 8-12. The lancet includes a housing 310, an operating button 312 and a firing mechanism 314 that is actuated by the operating button. An opening 316 is formed in the housing 310, and a tray 318 is receivable within the opening 316 for movement between open and closed positions. A piercing aperture 320 is formed through an end wall 322 of the tray 318, and a base portion 324 of the tray 318 is connected to the end wall 322 for receiving the lancet 304.

Figures 8, 9:
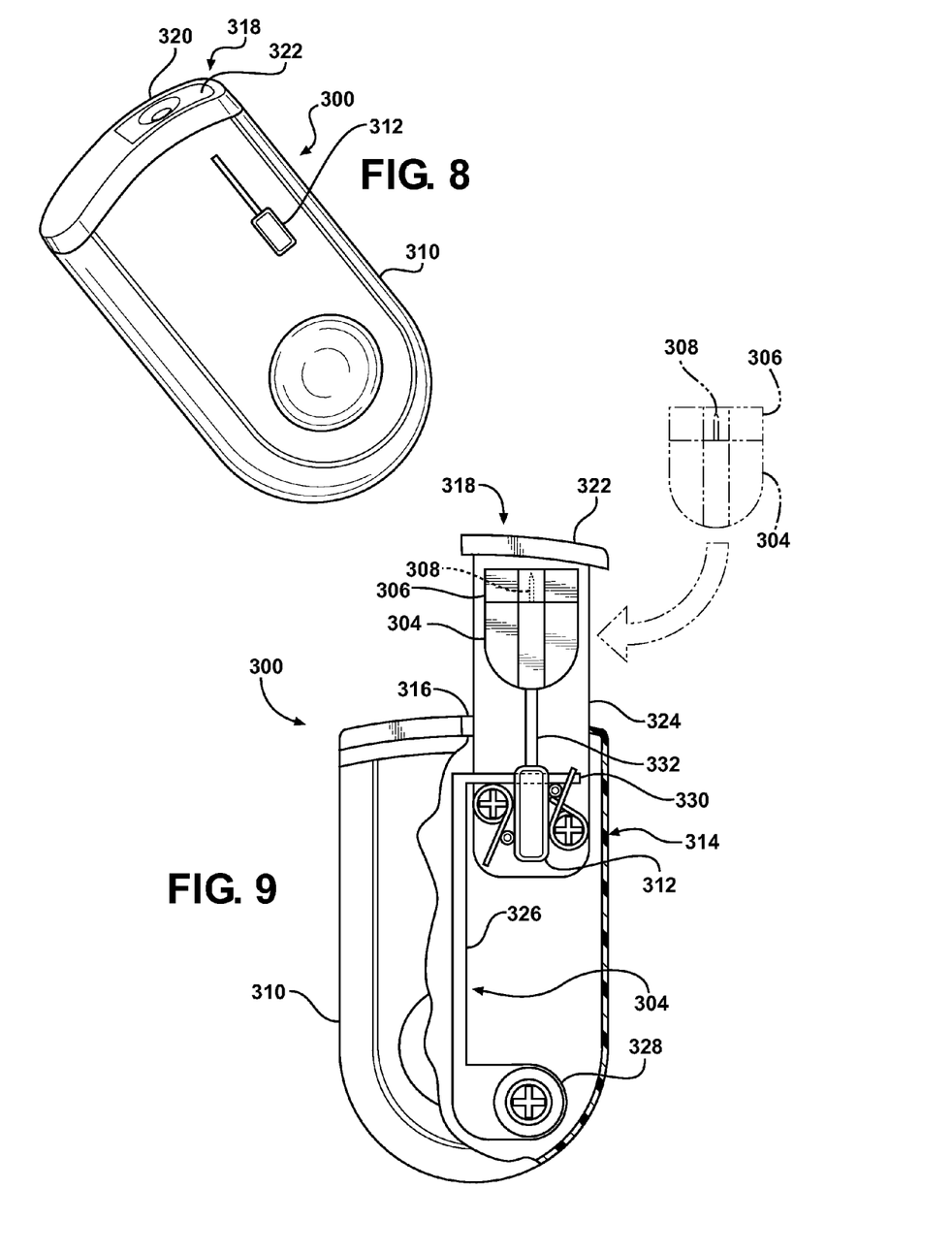
FIG. 8 is a perspective view of a lancing device in accordance with an embodiment of the invention.
FIG. 9 is a partial cross-section view of the lancing device of FIG. 8.

The decapping mechanism 302 is adapted to remove the cap 306 from the lancet 304 while the lancet 304 and the cap 306 are disposed within the housing 310 of the lancing device 300. The decapping mechanism 302 includes an arm portion 326 that is connected to the housing 310 by a pivot joint 328 to allow the decapping mechanism 302 to pivot between an operating position and a storing position. An engaging portion 330 is provided on the arm portion 326 opposite the pivot joint 328. The engaging portion 330 extends substantially perpendicular to the arm portion 326 and extends transversely across the base portion 324 of the tray 318 when the decapping mechanism 302 is in the operating position.

To install the lancet 304 in the lancing device 300, the tray 318 is moved to the open position and the lancet 304 is placed on the base portion 324 of the tray 318 in engagement with a firing rod 332 of the firing mechanism 314, as shown in FIG. 9. At this point, the cap 308 is seated on the sharp tip 306 of the lancet 304. The tray 318 is then moved to the closed position, which causes the engaging portion 330 of the decapping mechanism 302 to engage the cap 306, as shown in FIG. 10.

Figures 10, 11, 12:
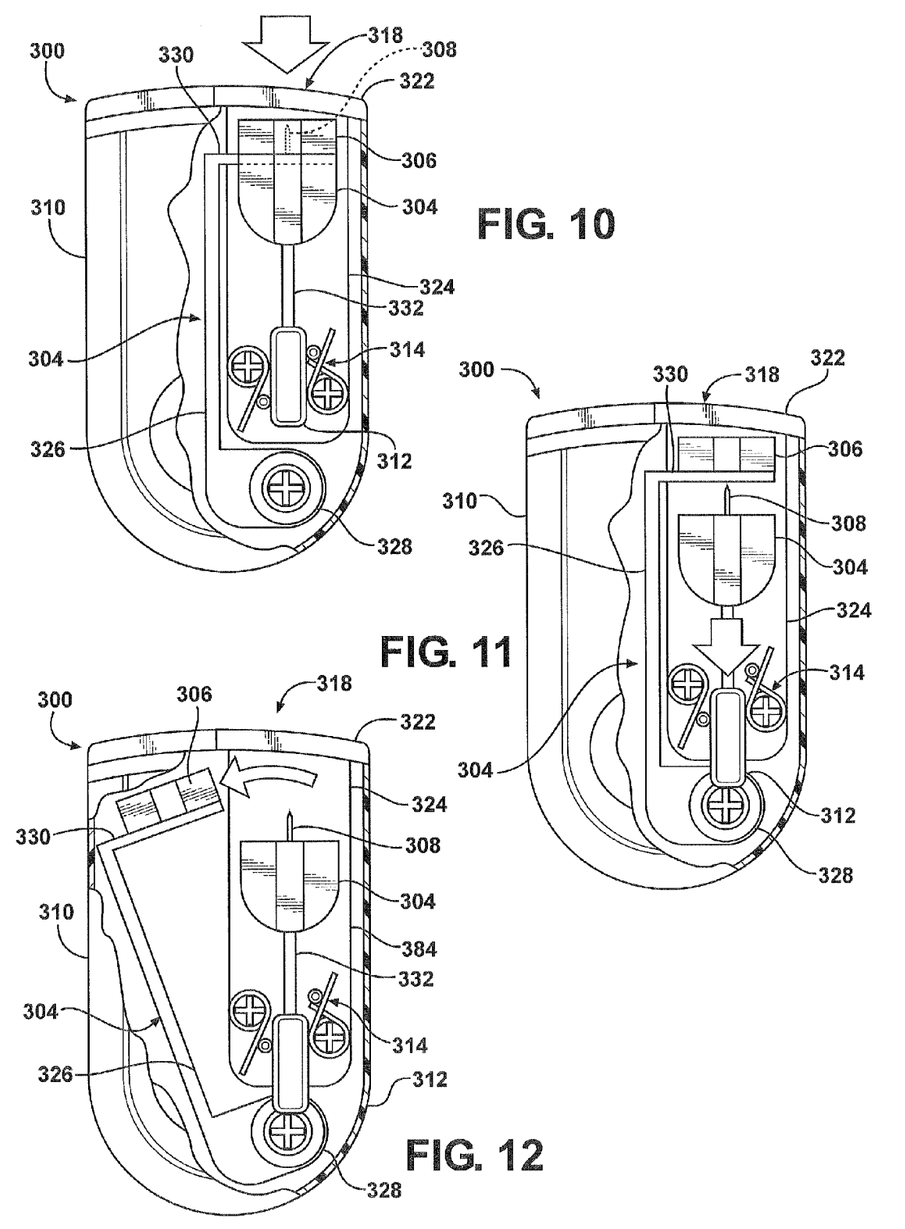
FIG. 10 is a partial cross-section view of the lancing device of FIG. 8.
FIG. 11 is a partial cross-section view of the lancing device of FIG. 8.
FIG. 12 is a partial cross-section view of the lancing device of FIG. 8.

As shown in FIG. 11, actuation of the operating button 312 moves the firing mechanism 314 to the cocked position, leaving the cap 306 connected to the engaging portion 330 of the decapping mechanism 302. The decapping mechanism 302 then moves to the storing position, so that the cap 306 is no longer disposed between the piercing aperture 320 and the sharp tip 308 of the lancet, so that the piercing operation can be performed, as shown in FIG. 12. After the piercing operation is completed, the decapping mechanism 302 returns to the operating position, and the cap 306 is replaced on the sharp tip 308 of the lancet 304.

Figure 13:
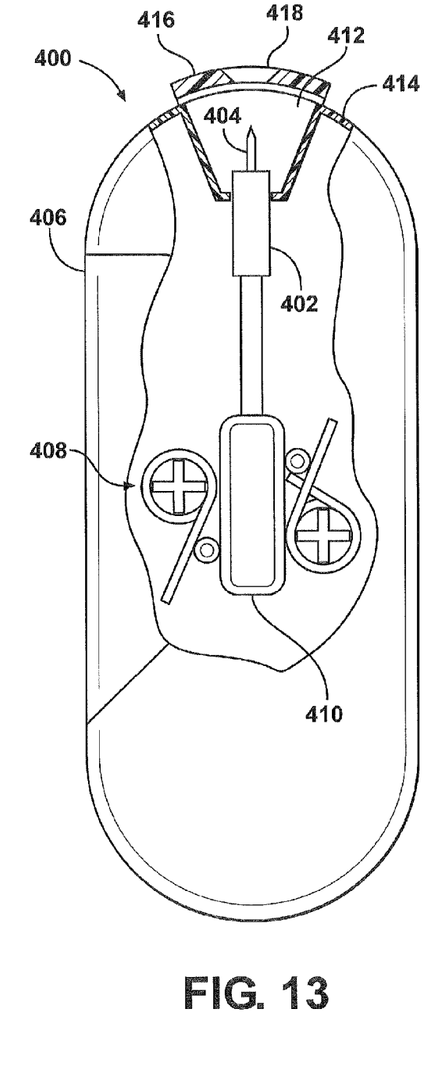
FIG. 13 is a top, cut-away view of a lancing device in accordance with an embodiment of the invention.
Figure 14:
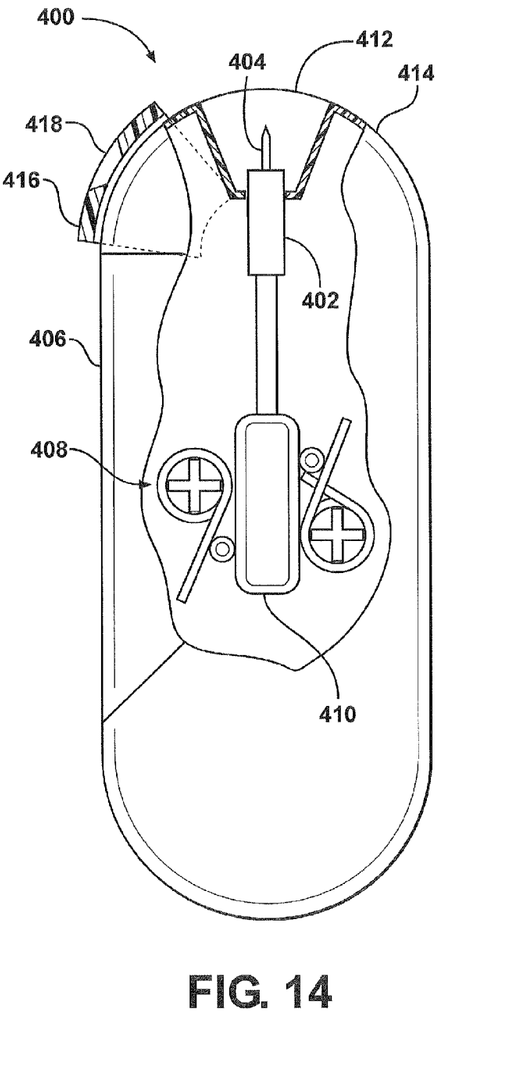
FIG. 14 is a top, cut-away view of a lancing device of FIG. 13.

In an another alternative embodiment, the invention provides a lancing device 400 for use with a lancet 402 having a sharp tip 404, as shown in FIGS. 13 and 14. The lancing device 400 includes a housing 406, a firing mechanism 408, and an operating button 410. The lancing device 400 allows control of the size of the piercing aperture, to allow samples to be collected from varied portions of the human body. In particular, an AST piercing aperture 412 is defined at a skin-engaging end 414 of the housing 406, and an aperture defining structure 416 having a nominal piercing aperture 418 is movably related to the housing. The nominal piercing aperture 418 is smaller than the AST piercing aperture 412, and the aperture defining structure 416 is configured to substantially cover and align with the AST piercing aperture 412 when the aperture defining structure 416 is in a use position, as shown in FIG. 13. When the aperture defining structure 416 is in a non-use position, the AST piercing aperture 412 is substantially unobstructed, as shown in FIG. 14. The skin engaging end 410 of the housing 406 could be substantially arcuate, and the aperture defining structure 416 could be pivotally mounted to the housing 406 to slide along the arcuate skin engaging end 410 of the housing 406 between the use and non-use positions. Furthermore, it should be understood that the aperture defining structure 416 could be provided on any of the lancing devices in the previously discussed embodiments.

The above-mentioned embodiments have been described in order to allow easy understanding of the present invention. The invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A lancing device for use with a removable lancet having a sharp tip, comprising:
 a housing having a longitudinal axis, a first housing end having an opening, a second housing end and an interior space in which the lancet can be received;
 a handle having a longitudinal axis, a first handle end and a second handle end, the handle connected to the housing at a location proximate both the second housing end and the second handle end for movement between a storage position where the first housing end is adjacent to the first handle end, the second housing end is adjacent the second handle end and the longitudinal axis of the housing and the longitudinal axis of the handle are parallel, and a use position, wherein the first housing end is located opposite the first handle end, the second housing end is adjacent the second handle end and the longitudinal axis of the housing and the longitudinal axis of the handle are parallel; and
 a tray that is receivable within the opening and on which the lancet can be removably retained and that is extendable from the opening such that the lancet can be accessed outside of the housing.

2. The lancing device of claim 1, further comprising:
 a piercing aperture located on the first housing end; and
 the first handle end substantially blocks the piercing aperture in the storage position.

3. The lancing device of claim 1, further comprising:
 the handle overlies at least part of the housing in the storage position to prevent insertion or removal of the lancet from the interior space.

4. The lancing device of claim 1,
 wherein the first handle end overlies at least part of the opening in the storage position to prevent removal of the tray from the housing.

5. The lancing device of claim 1, further comprising:
 the housing and the handle cooperate to define a first length in the storage position and a second length in the use position, and a third length longer than both the first length and second length when the tray is in an extended position.

6. The lancing device of claim 1, further comprising:
 the handle is pivotally connected to the housing for movement between the storage position and the use position.

7. The lancing device of claim 6, further comprising:
 a pivot joint formed at the second housing end; and
 the handle having a first leg pivotally connected to the housing by the pivot joint, a second leg pivotally connected to the housing by the pivot joint, and a third leg at the first handle end that spaces the first leg and the second leg, where the third leg is disposed at the first housing end in the storage position.

8. The lancing device of claim 1, further comprising:
 a structure attached to the tray and moveable with respect to the housing between a first position, where a first piercing aperture is defined, and a second position, where a second piercing aperture is defined, and the second piercing aperture is larger than the first piercing aperture.

9. A lancing device for use with a removable lancet having a sharp tip, comprising:
 a housing having an opening at a first end;
 a tray that is receivable within the opening and on which the lancet can be removably retained, the tray moveable with respect to the housing between an open position, where the lancet can be installed on or removed from the tray, and a closed position, where the lancet can be utilized to perform a piercing operation;
 a first piercing aperture through which the sharp tip protrudes during lancing formed through an end wall of the tray, wherein the end wall of the tray substantially occupies the opening of the housing when the tray is in the closed position; and a handle connected to the housing for movement between a storage position and a use position, where the housing and the handle cooperate to define a first length and one width in the storage position and a second length longer than the first length with the one width in the use position.

10. The lancing device of claim 9, further comprising:
the lancet including a cap configured to cover the sharp tip; and
at least one engaging member that engages the cap of the lancet when the tray is moved from the open position to the closed position, wherein engagement of the engaging member with the cap removes the cap from the sharp tip of the lancet.

11. The lancing device of claim 9, further comprising:
a carrier block that is engageable with the lancet to cover the sharp tip, the carrier block having a first engaging structure configured to allow disengagement of the lancet and the carrier block during installation of the lancet with respect to the lancing device, and a second engaging structure configured to permit engagement of the lancet and the carrier block during removal of the lancet from the lancing device and restrain the lancet against subsequent disengagement from the carrier block; and
an engaging member that is slidably connected to the housing and engageable with the lancet to remove the lancet from the first engaging structure of the carrier block.

12. The lancing device of claim 9, further comprising:
the handle is pivotally connected to the housing for movement between the storage position and the use position.

13. The lancing device of claim 9, further comprising:
a structure attached to the end wall of the tray and moveable with respect to the end wall between a first position, where the first piercing aperture is defined, and a second position, where a second piercing aperture through which the sharp tip protrudes is defined, and the second piercing aperture is larger than the first piercing aperture.

14. A lancing device for use with a removable lancet having a sharp tip, comprising:
a housing having an opening at a first end;
a tray that is receivable within the opening and on which the lancet can be removably retained, the tray moveable with respect to the housing between an open position, where the lancet can be installed on or removed from the tray, and a closed position, where the lancet can be utilized to perform a piercing operation;
a handle connected to the housing for movement between a storage position, where the housing and handle form a first length, and a use position, where the housing and handle form a second length longer than the first length; and
a structure connected to an end wall of the tray for movement between a first position, where the end wall and the structure cooperate to define a first piercing aperture through which the sharp tip protrudes, and a second position, where the end wall and the structure cooperate to define a second piercing aperture through which the sharp tip protrudes, the second piercing aperture larger than the first piercing aperture.

15. The lancing device of claim 14, further comprising:
the structure configured for movement to a third position where the structure blocks protrusion of the sharp tip of the lancet through both the first piercing aperture and the second piercing aperture.

16. The lancing device of claim 14, further comprising:
the structure slidably related to the tray.

17. The lancing device of claim 14, further comprising:
the handle overlies at least part of the opening in the storage position to prevent removal of the tray from the housing.

* * * * *